United States Patent
Bhullar et al.

(10) Patent No.: US 6,488,828 B1
(45) Date of Patent: Dec. 3, 2002

(54) RECLOSEABLE BIOSENSOR

(75) Inventors: Raghbir Singh Bhullar, Indianapolis, IN (US); Douglas Paul Walling, Indianapolis, IN (US); Brian S. Hill, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 58 days.

(21) Appl. No.: 09/620,191

(22) Filed: Jul. 20, 2000

(51) Int. Cl.[7] ............................................. G01N 27/327
(52) U.S. Cl. ............................ 204/403.01; 204/403.04; 204/403.14
(58) Field of Search ...................... 204/403, 403.04, 204/403.14, 403.01

(56) References Cited

U.S. PATENT DOCUMENTS

| | | |
|---|---|---|
| 4,600,745 A | 7/1986 | Creighton |
| 4,963,814 A | 10/1990 | Parks et al. |
| 4,999,582 A | 3/1991 | Parks et al. |
| 4,999,632 A | 3/1991 | Parks |
| 5,243,516 A | 9/1993 | White |
| 5,352,351 A | 10/1994 | White et al. |
| 5,366,609 A | 11/1994 | White et al. |
| 5,393,391 A * | 2/1995 | Dietze et al. ............... 204/403 |
| 5,405,511 A | 4/1995 | White et al. |
| 5,413,690 A | 5/1995 | Kost et al. |
| 5,438,271 A | 8/1995 | White et al. |
| 5,441,698 A | 8/1995 | Norell |
| 5,628,890 A | 5/1997 | Carter et al. |
| 5,630,986 A | 5/1997 | Charlton et al. |
| 5,741,634 A | 4/1998 | Nozoe et al. |
| 5,747,351 A | 5/1998 | Hemmati |
| 5,762,770 A | 6/1998 | Pritchard et al. |
| 5,788,064 A | 8/1998 | Sacherer et al. |
| 5,798,031 A | 8/1998 | Charlton et al. |
| 5,812,312 A * | 9/1998 | Lorinez ..................... 359/397 |
| 5,855,434 A | 1/1999 | Hagen |
| 5,856,195 A | 1/1999 | Charlton et al. |
| 5,888,826 A | 3/1999 | Ostgaard et al. |
| 5,962,333 A | 10/1999 | Incorvia et al. |
| 5,985,675 A | 11/1999 | Charm et al. |
| 6,027,693 A * | 2/2000 | Molina et al. ................ 422/98 |
| 6,033,627 A * | 5/2000 | Shields et al. ................ 422/58 |
| 6,125,292 A * | 9/2000 | Uenoyama et al. ......... 600/345 |

FOREIGN PATENT DOCUMENTS

| | | |
|---|---|---|
| WO | WO 97/27483 | 7/1997 |
| WO | WO 99/30152 | 6/1999 |
| WO | WO 99/34191 | 7/1999 |

\* cited by examiner

*Primary Examiner*—Robert J. Warden, Sr.
*Assistant Examiner*—Kaj K. Olsen
(74) *Attorney, Agent, or Firm*—Jill L. Woodburn

(57) ABSTRACT

A recloseable biosensor is provided that comprises a substrate, a sample site positioned on the substrate, and an openable and recloseable cover coupled to the substrate. The cover is operative to selectively block access to the sample site. The cover includes a fixed end coupled to the substrate, an opposite free end, and a middle portion extending across the sample site. The middle portion is releasably and recloseably adhered to the substrate.

14 Claims, 10 Drawing Sheets

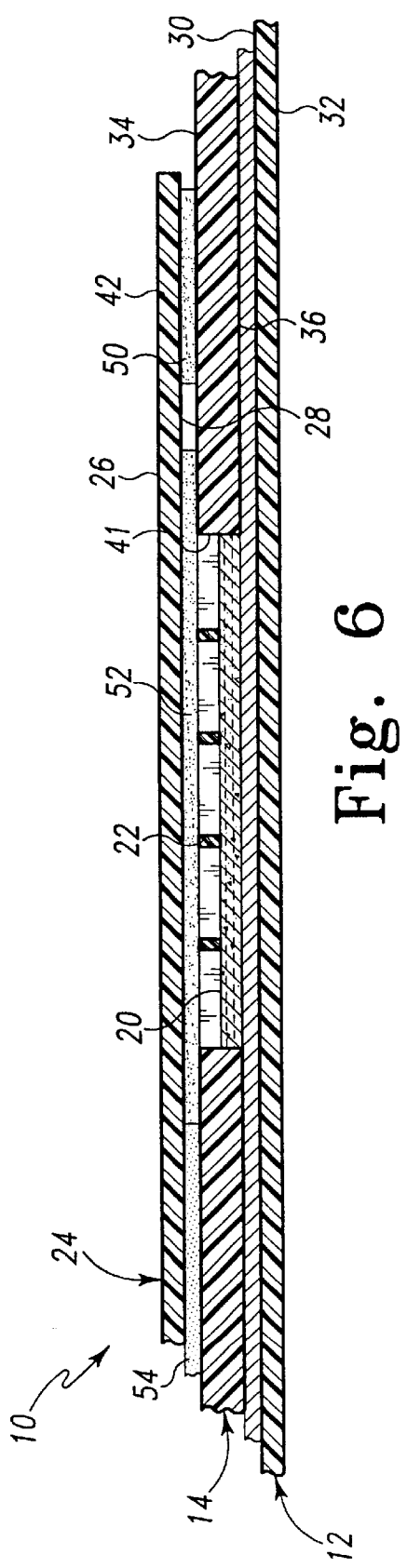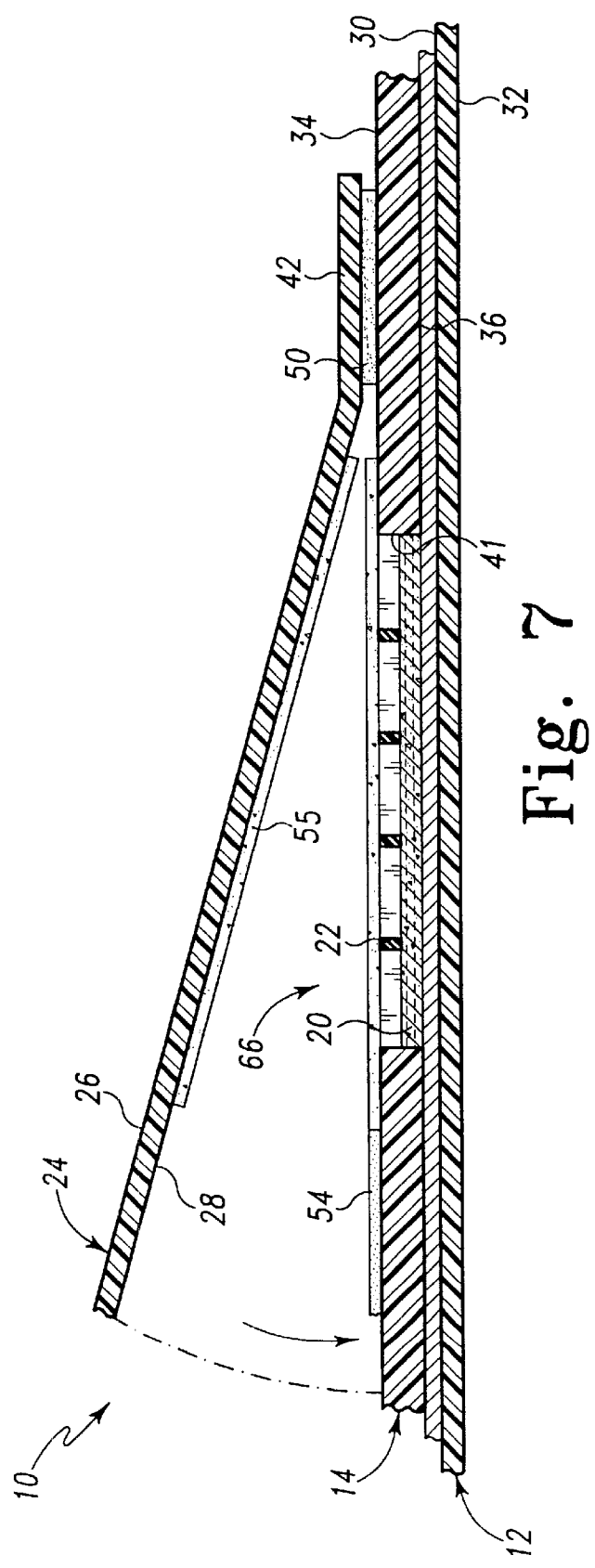

US 6,488,828 B1

RECLOSEABLE BIOSENSOR

FIELD OF THE INVENTION

The present invention relates to a biosensor for use in determining the concentration of an analyte in a sample.

BACKGROUND AND SUMMARY OF THE INVENTION

Electrochemical biosensors are known. They have been used to determine the concentration of various analytes from biological samples, particularly from blood. Biosensors are described in U.S. Pat. Nos. 5,288,636; 5,413,690; 5,762,770; 5,798,031; and 5,997,817, the disclosure of each of which are hereby incorporated by reference. Storage containers for test strips are also known. See U.S. Pat. Nos. 5,788,064 and 5,985,675.

According to the present invention, a recloseable biosensor is provided that comprises a substrate having a top surface, a reagent positioned on the top surface, and an openable and recloseable cover including a first fixed end coupled to the substrate, an opposite second free end, and a middle portion extending between the opposite ends across the reagent. The cover is operative to selectively block access to the reagent.

In addition, according to the invention a recloseable biosensor is provided that comprises a substrate including a sample site, a reagent positioned at the sample site, and a cover extending across the reagent. The cover is releasably and recloseably coupled to the substrate.

Further, according to the invention a recloseable biosensor is provided that comprises a substrate formed to include a sample site and a cover. The cover includes first and second ends and a middle portion that extends between the ends. The first end is coupled to the substrate and the middle portion extends over the sample site and is releasably and recloseably coupled to the substrate.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 6 is a view taken along lines 7—7 of FIG. 2;

FIG. 7 is a view similar to FIG. 6 following movement of the cover away from the substrate;

DETAILED DESCRIPTION OF THE DRAWINGS

Figure 1:
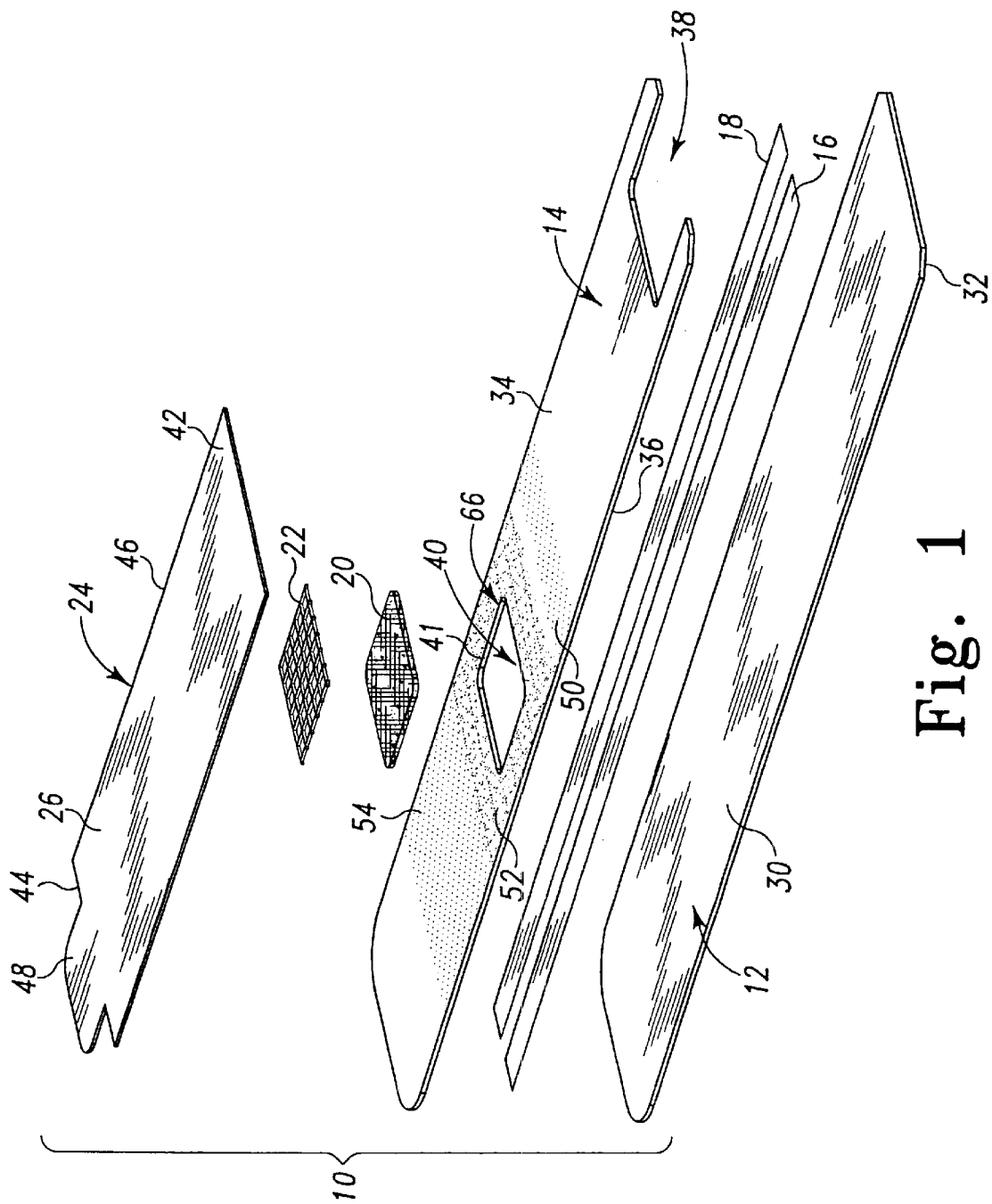
FIG. 1 is an exploded perspective view of a biosensor of the present invention.
Figure 2:
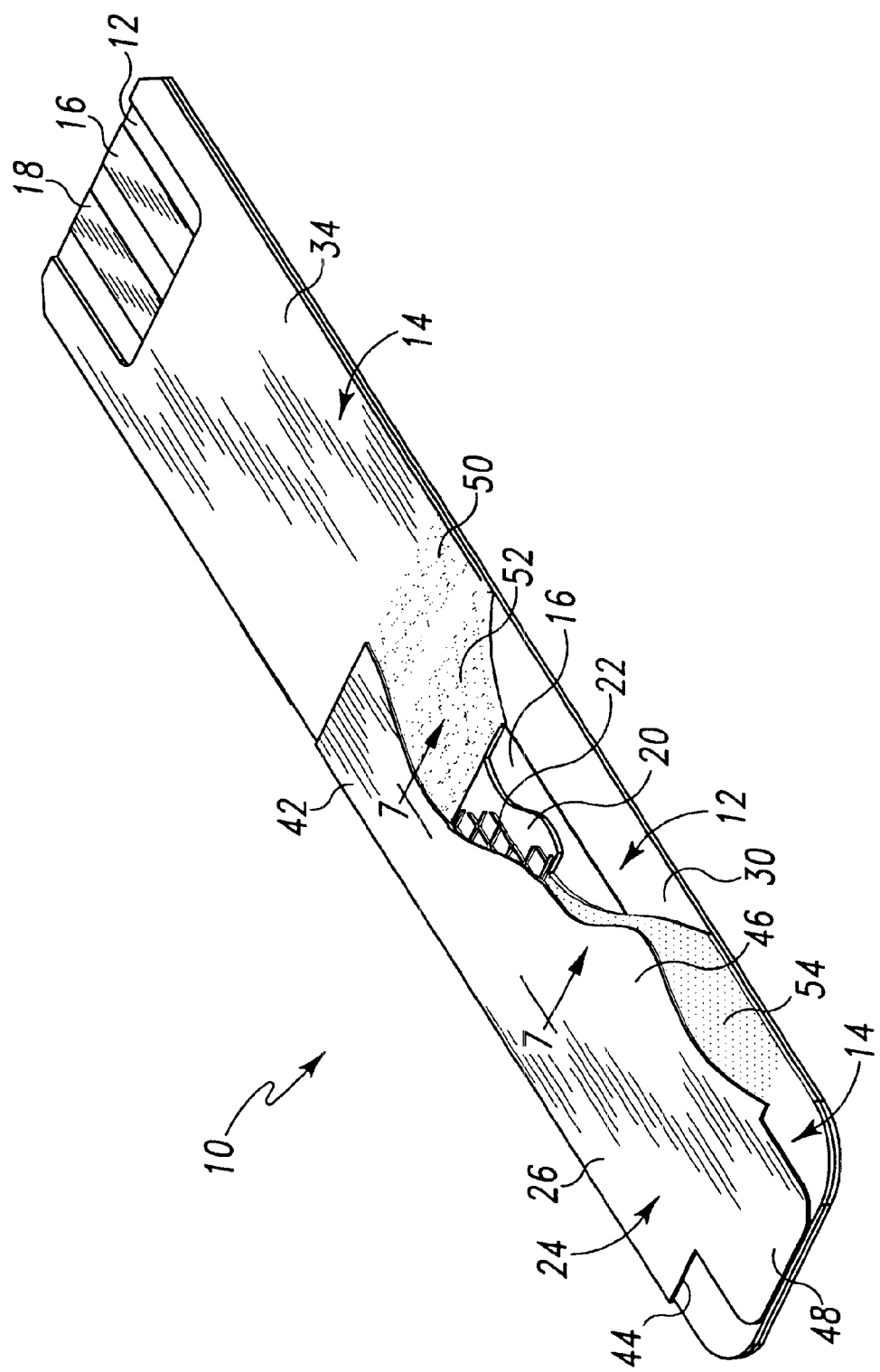
FIG. 2 is a perspective view of the biosensor of FIG. 1 with portions broken away.
Figure 3:
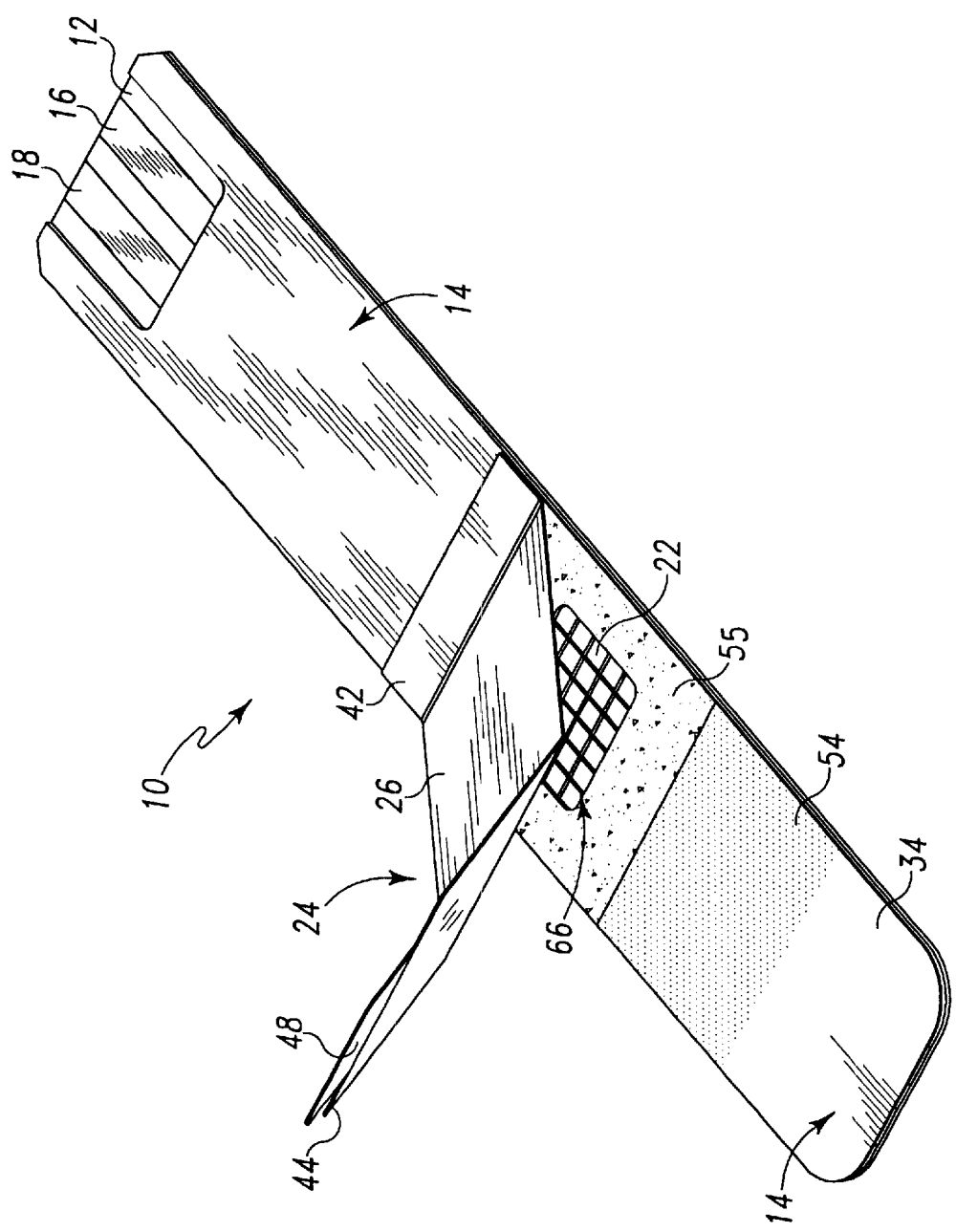
FIG. 3 is a perspective view of the biosensor of FIG. 2 following movement of the cover away from the substrate.

The present invention relates to a recloseable biosensor that can be closed after the initial opening to protect a sample site. Thus, the need to locate a storage container for the biosensor either prior to use or before disposal is avoided. As such, providing biosensors with recloseable covers appreciably enhances the marketability and environmental friendliness of the biosensor. Various aspects of the invention are presented in FIGS. 1–11, which are not drawn to scale and wherein like components in the several views are numbered alike.

FIGS. 1–7 illustrate an aspect of the invention in the form of biosensor 10 having a first insulating substrate 12, a second insulating substrate 14, electrically conductive tracks 16, 18 situated between substrates 12, 14, a testing reagent 20, spreading mesh 22, and a cover 24 positioned over reagent 20 and mesh 22. Biosensor 10 is produced from rolls of material. Thus, the selection of materials for the construction of biosensor 10 necessitates the use of materials that are sufficiently flexible for roll processing, but which are still rigid enough to give a useful stiffness to finished biosensor 10.

First substrate 12 of biosensor 10 includes a first surface 30 that supports conductive tracks 16, 18 and an opposite second surface 32. See FIG. 1. First substrate 12 may be constructed from a wide variety of insulative materials. Non-limiting examples of insulative materials that provide desirable electrical and structural properties include vinyl polymers, polyimides, polyesters, and styrenics. Preferably, first substrate 12 is 7 mil thick MELINEX 329 plastic, a polyester commercially available from E.I. DuPont de Nemours, Wilmington, Del.

As shown in FIGS. 1–5, electrically conductive tracks 16, 18 are laid down onto first surface 30 of first substrate 12. Tracks 16, 18 represent the electrodes of biosensor 10. Therefore, track 16 may be a working electrode and track 18 may be an auxiliary electrode. The distance between tracks 16, 18 is about 1.2 millimeters (mm). It is appreciated that the distance between tracks 16, 18 may vary in accordance with this disclosure.

Tracks 16, 18 are constructed from electrically-conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks 16, 18 include gold, platinum, palladium, iridium, or alloys of these metals, since such noble metals and their alloys are unreactive in biological systems. Most preferably, track 16 is a working electrode made of platinum, and track 18 is an auxiliary electrode that is also made of platinum and is substantially the same size as the working electrode. Tracks 16, 18 are deposited on an insulative backing (not shown), such as polyimide or polyester. An example of such an insulator is the polyimide UPILEX from UBE INDUSTRIES, LTD., Japan, which is available pre-coated with gold, palladium or platinum from TECHNI-MET of Connecticut, USA.

Three electrode arrangements are also possible, wherein biosensor 10 includes an additional electrically conductive track (not shown). In a three-electrode arrangement, track 16 is a working electrode, track 18 is a counter electrode, and the third electrode is a reference electrode. It is also appreciated that a three-electrode arrangement is possible where tracks 16 and 18 are working electrodes and a third electrode is provided as an auxiliary or reference electrode in accordance with this disclosure.

Second substrate 14 of biosensor 10 overlaps tracks 16, 18. Second substrate 14 has a first surface 34 and a second surface 36 facing conductive tracks 16, 18. As shown in FIG. 1, second substrate 14 is formed to include first and second openings 38, 40. First opening 38 exposes portions of tracks 16, 18 for electrical connection with a meter (not shown), which measures some electrical property of a liquid sample 133 (FIG. 5) after sample 133 is applied to reagent 20 of biosensor 10. Second opening 40 includes an edge 41 that defines a perimeter of a sample site 66. Sample site 66 can take on a variety of shapes and sizes to aid a user in identifying where to deposit the liquid sample 133 in accordance with this disclosure. Second substrate 14 is coupled to first substrate 12 and tracks 16, 18 by an adhesive such as a hot melt glue. A non-limiting example of such glue is DYNAPOL S-1358 glue, available from Hüils America, Inc., 220 Davidson Street, P.O. Box 6821, Somerset, N.J. 08873. It is appreciated that first and second substrates 12, 14 may be coupled together using a wide variety of commercially available adhesives or with welding (heat or ultrasonic) in accordance with this disclosure.

Second opening 40 of second substrate 14 is positioned to expose a portion of tracks 16, 18 for application of reagent 20 to those exposed surfaces of tracks 16, 18. See FIGS. 1–2. The length and width of opening 40 define the length and width of sample site 66 and the thickness of second substrate 14 defines the height of a test chamber. Sample site 66 is formed as a rectangle of about 4.0 mm on one side and about 4.2 mm on the other side. The degree to which tracks 16, 18 are exposed determines the surface area for each electrode. The working and auxiliary electrodes 16, 18 each have substantially equivalent surface areas of about 6 mm$^2$. It is appreciated, however, that the degree of exposure of tracks 16, 18 may vary in accordance with this disclosure.

Reagent 20 provides electrochemical probes for specific analytes and is positioned in test chamber 66 such that reagent 20 covers working electrode 16. Reagent 20 is placed as a film of generally uniform thickness over first surface 30 in test chamber 66 and across electrodes 16, 18. Reagent 20 will then present a hydrophilic surface to the interior of test chamber 66.

After drying, reagent mesh 22, which has been impregnated with a surfactant, is placed over opening 40. Mesh 22 is preferably a polyester monofilament mesh from Sefar America, Inc. 333 S. Highland Avenue, Briarcliff Manor, N.Y. Mesh 22 is preferably dipped in a solution of 0.8% (wt:vol) dioctylsodium sulfosuccinate (DONS) in a solution of 50:50 (vol.:vol.) methanol : water and then dried. It is appreciated that biosensor 10 may be constructed using a variety of commercially available meshes or may even be constructed without mesh in accordance with this disclosure.

The choice of specific reagent 20 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilodaltons), 3.3 mg NATROSOL 250M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is incorporated herein by reference.

Non-limiting examples of enzymes and mediators that may be used in measuring particular analytes in sensor 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |

TABLE 1-continued

| Analyte | Enzymes | Mediator (Oxidized Form) | Additional Mediator |
|---|---|---|---|
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of sample 133 may be accurately correlated to the concentration of the analyte in sample 133 with biosensor 10 in accordance with this disclosure.

Figure 4:
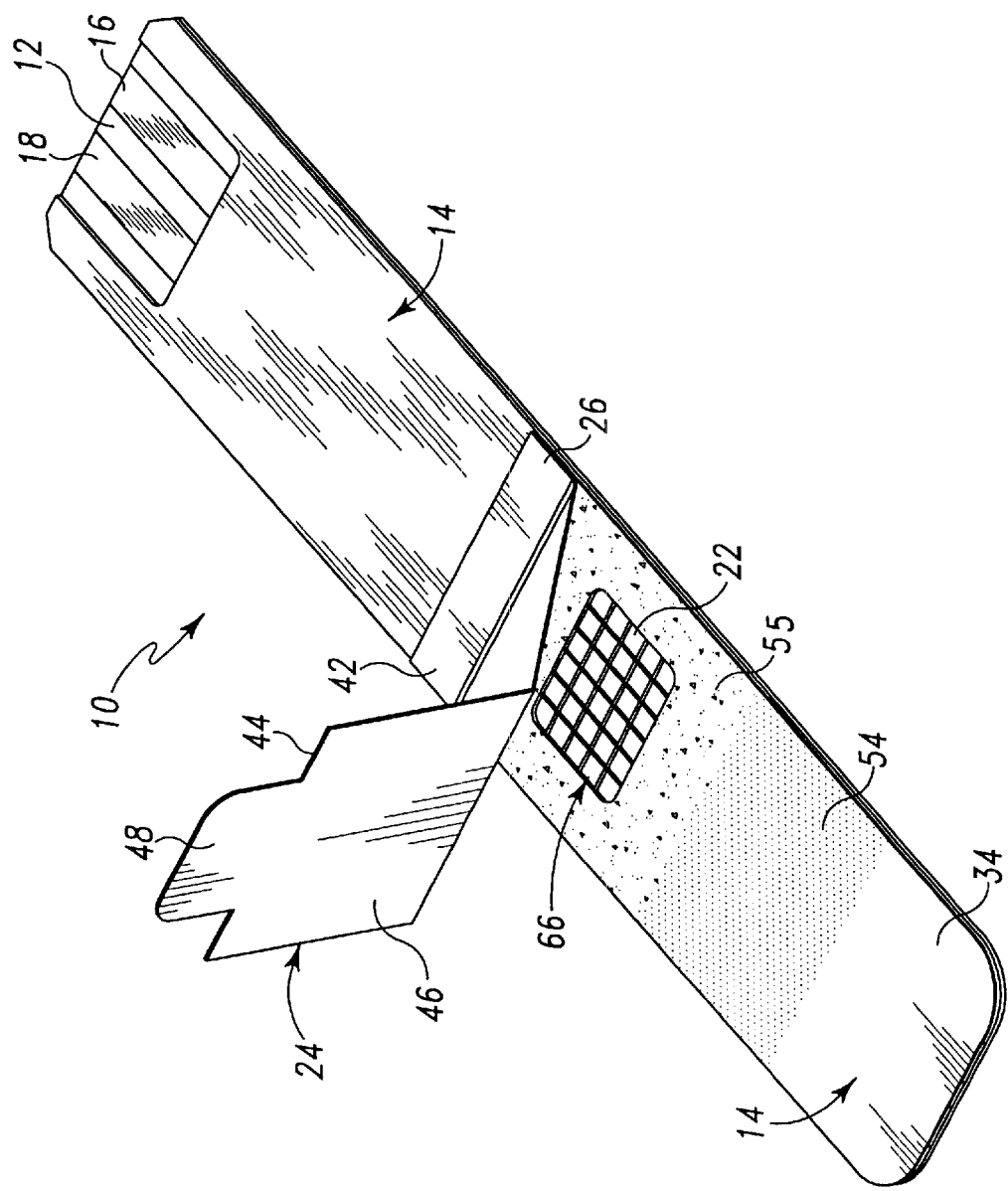
FIG. 4 is a view similar to FIG. 3 following additional movement of the cover away from the substrate.
Figure 5:
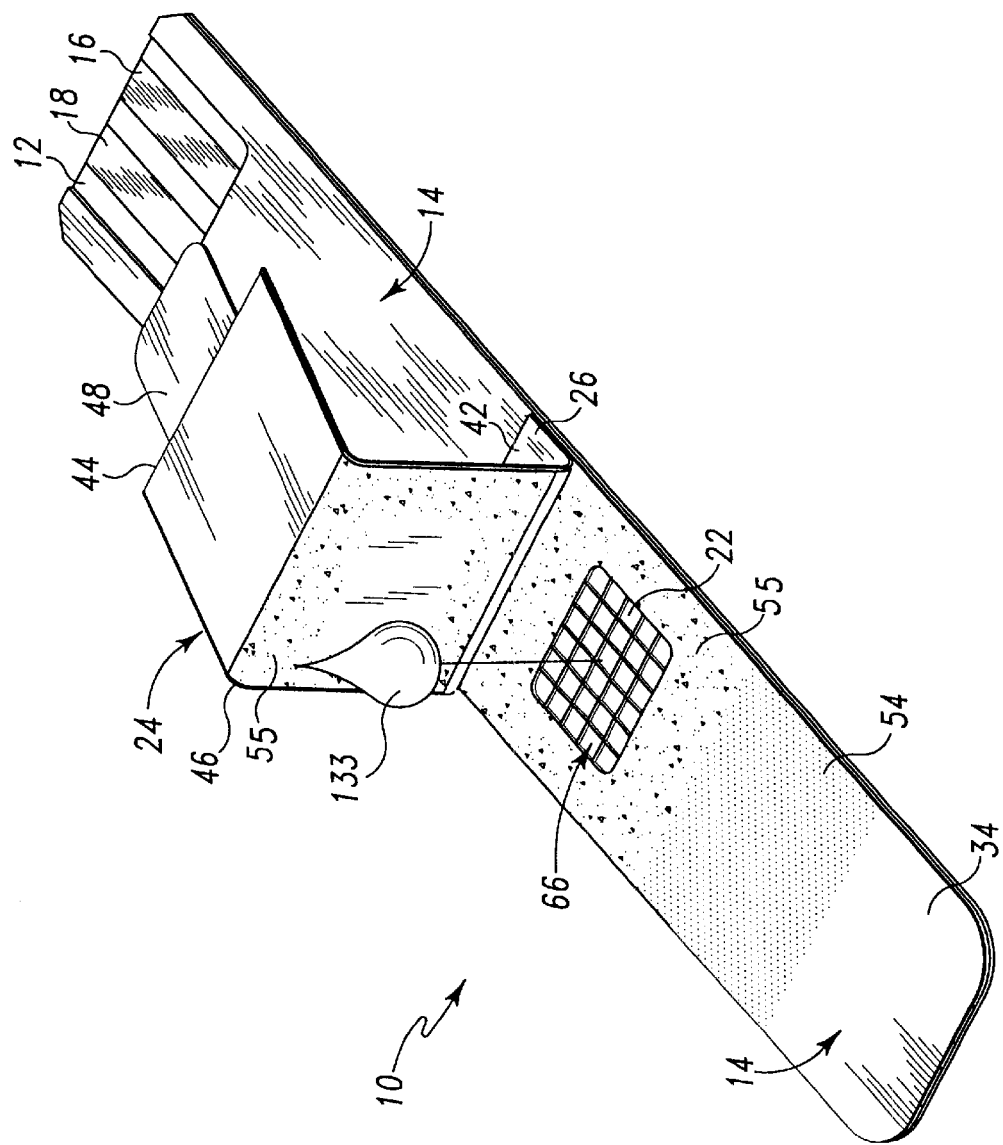
FIG. 5 is a view similar to FIG. 4 following additional movement of the cover to an opened position.

As shown in FIGS. 1–7, cover 24 overlays a portion of second substrate 14 and sample site 66 to protect reagent 20 from the surrounding environment prior to use. Following use, cover 24 overlays sample site 66 to block exposure of the reagent/sample mixture to the surrounding environment. Referring specifically to FIGS. 4–5, cover 24 includes a top side 26 and a bottom side 28 that engages first surface 34 of second substrate 14. Cover 24 further includes a fixed end 42 coupled to first surface 34 of second substrate 14, an opposite free end 44, and a middle portion 46 that extends between opposite ends 42, 44 across sample site 66 and reagent 20.

Cover 24 is constructed of a material with a relatively high tear resistance, such as a metallized polyester foil that has a thickness of about 2 mil (0.05 mm) to 6 mil (0.15 mm) thickness. It is appreciated, however, that cover 24 may be constructed from a variety of commercially available flexible polymers that are suitable for reducing the transmission of light and are relatively impermeable to moisture and gas in accordance with this disclosure. Non-limiting examples of suitable materials for use as cover 24 include polyimide, polyolefins, poly (vinyl chloride), poly (ethylene terephthalate), and polypropylene. Additionally, while not illustrated, it is appreciated that top side 26 of cover 24 may be printed with, for example, product labeling or instructions for use in accordance with this disclosure.

As shown in FIGS. 6–7, an adhesive 50 permanently bonds fixed end 42 of cover 24 to second substrate 14 and an adhesive 52 creates an initial seal about sample site 66. Unless indicated otherwise, the term "permanent" is used herein to mean continuing or enduring without findamental or marked change. Still further, an adhesive 54 releasably secures middle portion 46 of cover 24 to second substrate 14. Adhesive 50, which couples fixed end 42 of cover 24 to second substrate 14 is preferably a hot-melt adhesive. Adhesive 50 is distributed over first surface 34 of second substrate 14 and/or the adjacent bottom side 28 of fixed end 42. Adhesive 50 adheres fixed end 42 to second substrate 14 after cover 24 is applied to first surface 34, so that in normal usage of biosensor 10, fixed end 42 stays adhered to second substrate 14. More specifically, the adhesive bond between fixed end 42 and first surface 34 is intended to never be broken. Non-limiting examples of suitable hot-melt adhesives are HL-7276, an ethyl vinlyacetate adhesive and HL-0705-S, an olefin adhesive, both of which are commercially available from H.B. Fuller Company, St. Paul, Minn. It is appreciated that a wide variety of hot-melt adhesives that are designed for case and carton sealing as well as welding (heat or ultrasonic) may be used to couple fixed end 42 onto second substrate 14.

Middle portion 46 of cover 24 is coupled to second substrate 14 by first and second adhesives 52, 54. First adhesive 52 is distributed over first surface 34 of second substrate 14 spaced-apart from adhesive 50 and/or the adjacent bottom side 28 of middle portion 46. First adhesive 52 adheres middle portion 46 to second substrate 14 after cover 24 is applied to first surface 34, so that in normal usage of biosensor 10, the adhesive bond between middle portion 46 and first surface 34 is broken once just prior to use. Thus, a seal is established between cover 24 and second substrate 14 around reagent 20 during storage of biosensor 10. As shown in FIG. 5, once seal is broken, a film 55 is generally left on first surface 34 and/or cover 24 such that adhesive 52 will not reseal cover 24 and second substrate 14. Non-limiting examples of suitable hot-melt adhesives are HL-7276, an ethyl vinlyacetate adhesive and HL-0705-S, an olefin adhesive, both of which are available from H.B. Fuller Company, St. Paul, Minn. It is appreciated that a wide variety of hot-melt adhesives that are designed for case and carton sealing as well as welding (heat or ultrasonic) may be used to couple fixed end 42 onto second substrate 14.

Middle portion 46 of cover 24 is also coupled to second substrate 14 by second adhesive 54. Second adhesive 54 is a pressure-sensitive, releasable, resealable adhesive, which serves to hold middle portion 46 of cover 24 against second substrate 14. Adhesive 54 may be permanently applied to second substrate 14 and/or to cover 24. As illustrated, adhesive 54 is permanently applied to second substrate 14 so that the seal between second adhesive 54 and cover 24 is broken when free end 44 of cover 24 is lifted away from second substrate 14.

A suitable pressure-sensitive adhesive 54 for use with biosensor 10 can be resealed against cover 24 so that cover 24 extends across sample site 66. Second adhesive 54 is preferably spaced-apart from the end of substrate 14 that is in general alignment with a tab 48 that extends from free end 44 of cover 24. Tab 48 is easily grasped by the user to enable the user to selectively lift middle portion 46 of cover 24 away from second substrate 14, as shown in FIGS. 3–5 and 7. A non-limiting example of a suitable pressure-sensitive adhesive 54 is HL-2268, commercially available from H.B. Fuller Company, St. Paul, Minn. It is appreciated that a wide variety of pressure-sensitive adhesives as well as, hook-and-loop type fasteners, tongue and groove fasteners, and the like may be used to affix middle portion 46 on second substrate 14.

Biosensor 10 incorporating reagent 20 of the present invention is preferably manufactured using rolls of materials, which are wider than the biosensor itself. Specifically, first substrate 12, tracks 16, 18, and second substrate 14 are assembled as described in U.S. Pat. No. 5,762,770, the disclosure of which is incorporated herein by reference and situated in a roll 68. Roll 68 is unwound and holt-melt adhesives 50, 52 and pressure-sensitive adhesive 54 are applied to first surface 34 of second substrate 14 using a computer controlled hot melt dispense unit 101. It is appreciated that a number of commercially available dispense units may be used to apply adhesives 50, 52, 54 onto second substrate 14 in accordance with this disclosure. It is also appreciated that one of ordinary skill in the art will appreciate that first substrate 12, tracks 16, 18, and second substrate 14 may be assembled using a variety of known manufacturing techniques.

Figure 8:
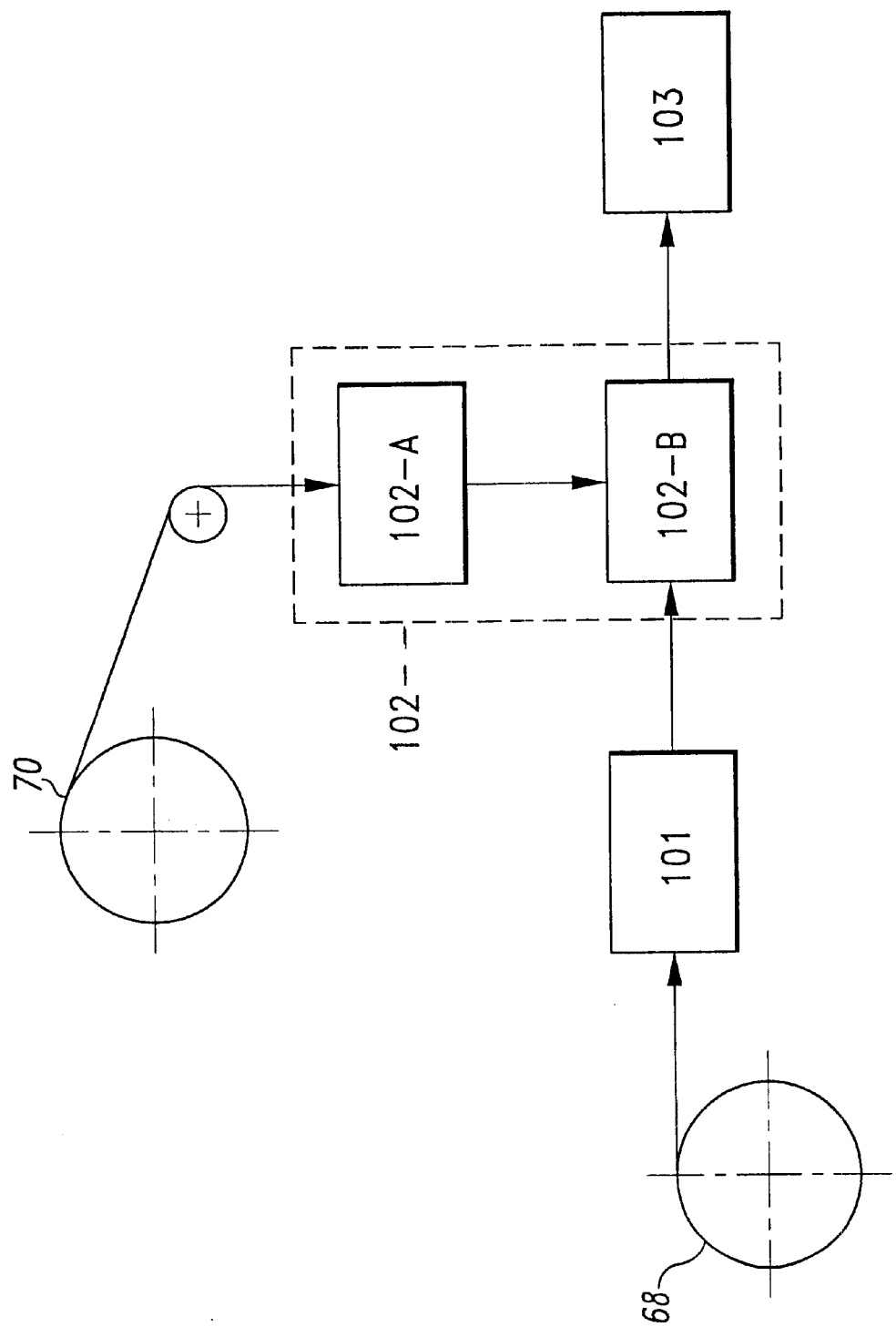
FIG. 8 is a diagrammatic view showing assembly of the biosensor of FIGS. 1–7.

Cover 24 is also situated in a roll 70, as shown in FIG. 8, which is wider than the cover itself. Roll 70 is unwound and fed into a slitting station 102a of a cutting unit 102. In slitting station 102a, cover material of roll 70 is slit into the appropriate width for each biosensor 10. Additionally, cover material of roll 70 is fed into cut/punch & placement unit 102b of cutting unit 102. In unit 102b, contours of tab 48 and cover 24 are punched from cover material of roll 70 and the resulting covers are placed upon adhesives 50, 52, 54 to form a series of attached biosensors. These attached biosensors are then fed into a sensor punch unit 103, where the attached biosensors are cut to form individual biosensors 10. It is appreciated that any number of commercially available dispense units, cutting units, and sensor punch units may be used to form biosensor 10 in accordance with this disclosure.

A plurality of biosensors are typically packaged in a vial, usually with a stopper formed to seal the vial. It is appreciated, however, that biosensors may be packaged individually, or biosensors can be folded upon one another, rolled in a coil, stacked in cassette magazine, or packed in a blister packaging.

Biosensor 10 is used in conjunction with the following:
1. a power source in electrical connection with the working and auxiliary electrodes and capable of supplying an electrical potential difference between the working and auxiliary electrodes sufficient to cause diffusion limited electro-oxidation of the reduced form of the mediator at the surface of the working electrode; and
2. a meter in electrical connection with the working and auxiliary electrodes and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

In use, the user lifts tab 48 to separate middle portion 46 of cover 24 from second substrate 14 and open sample site 66 to view. See FIGS. 3–5. A liquid sample 133 is then deposited on sample site 66. When reagent 20 is the reagent for measuring glucose as described above, sample 133 containing the analyte dissolves reagent 20 in opening 40 to oxidize the analyte and reduce the oxidized form of the mediator. The reaction between the analyte and reagent 20 is permitted to go to completion. (Completion is defined as sufficient reaction involving analyte, enzyme, and mediator (oxidized form) to correlate analyte concentration to diffusion limited current generated by oxidation of the reduced form of the mediator at the surface of the working electrode.)

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode. The measured current may be accurately correlated to the concentration of the analyte in sample 133 when the following requirements are satisfied:

1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

Once the concentration of the analyte is determined, the user presses the middle portion 46 of cover 24 over sample site 66 to reclose cover 24 onto second substrate 14. Thus, recloseable cover 24 provides a protective covering for sample site 66 during storage before use and prior to disposal following completion of the assay to seal sample 133 in biosensor 10.

Figure 9:
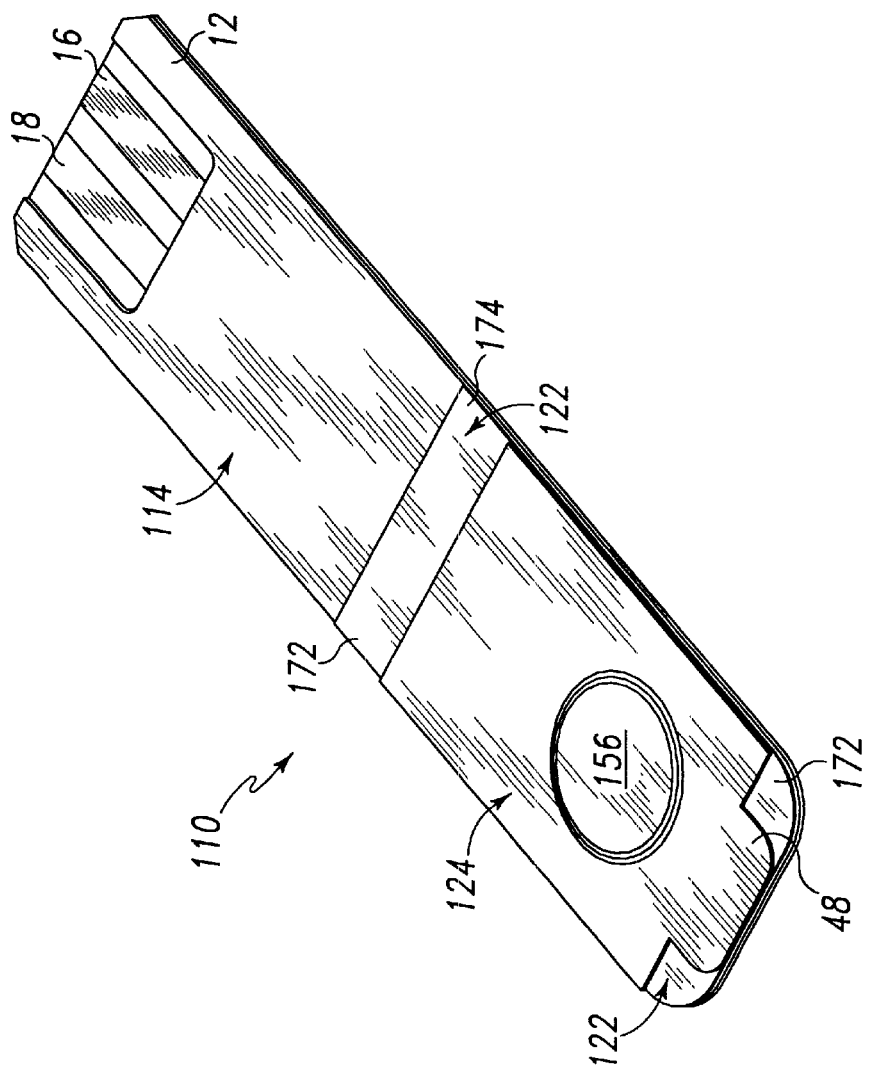
FIG. 9 is a perspective view of a biosensor according to a further aspect of the invention showing a cover positioned on a substrate in a sealed position.
Figure 10:
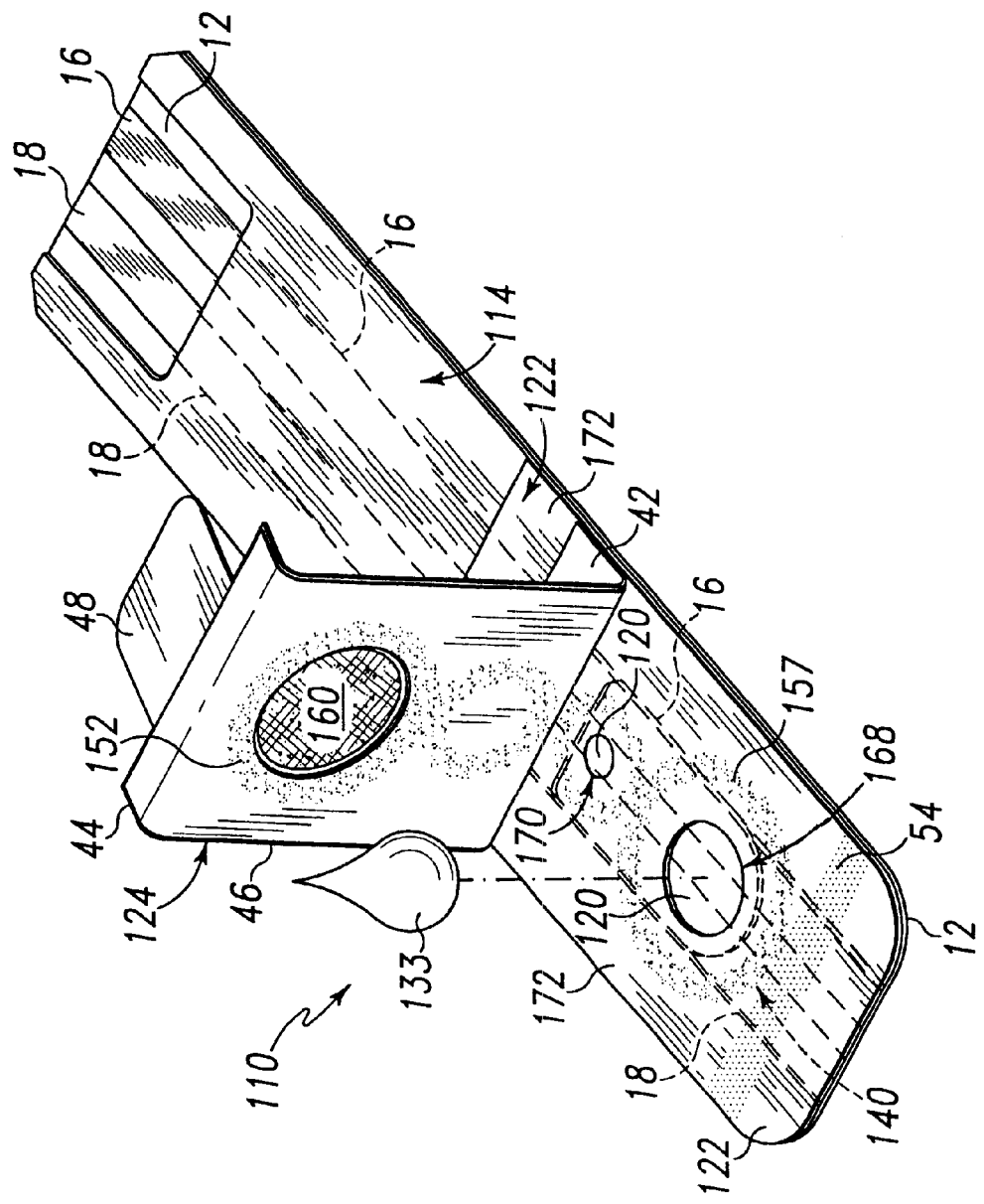
FIG. 10 is a view similar to FIG. 9 with portions broken away following movement of the cover away from the substrate to an opened position.
Figure 11:
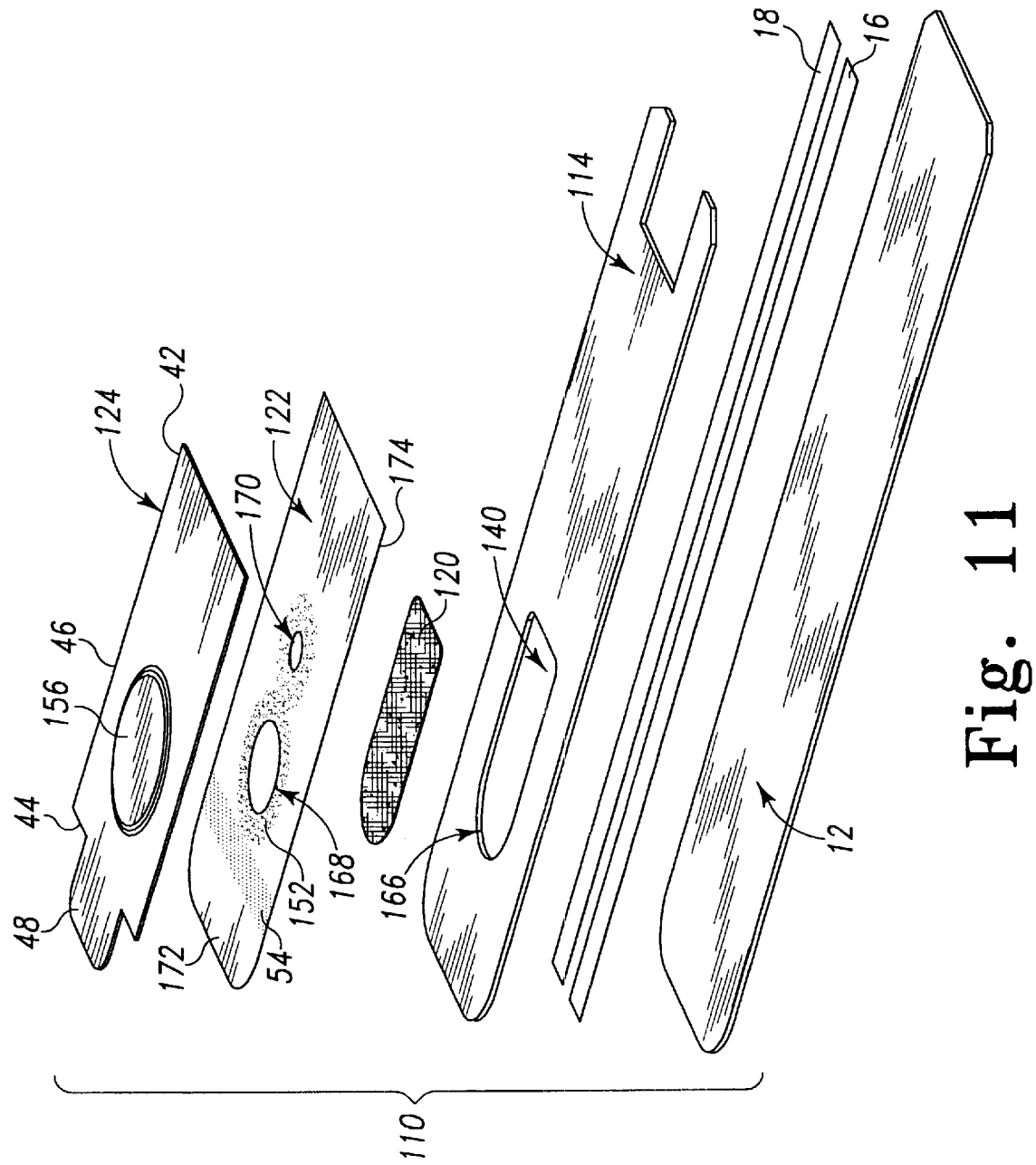
FIG. 11 is an exploded perspective view of the biosensor of FIG. 9.

A biosensor 110 is provided in accordance with another aspect of this invention and is illustrated in FIGS. 9–11. Biosensor 110 includes a second insulating substrate 114 situated on first substrate 12, tracks 16, 18 situated between substrates 12, 114, a testing reagent 120, a third substrate 122 situated over reagent 120 on a portion of second substrate 114, and a cover 124 that extends over third substrate 122. Biosensor 110 is produced from rolls of material in a manner similar to biosensor 10.

Referring now to FIG. 11, second substrate 114 is formed to include a channel 140 that is sized to receive reagent 120 and defines a sample site 166. Reagent 120 is formed similarly to reagent 20, except for its shape. Reagent 120 and sample site 166 can take on a variety of shapes and in accordance with this disclosure. Second substrate 114 is coupled to first substrate 12, tracks 16, 18, and third substrate 122 by an adhesive such as a hot melt glue. A non-limiting example of such glue is DYNAPOL S-1358 glue, available from Hüils America, Inc., 220 Davidson Street, P.O. Box 6821, Somerset, N.J. 08873. It is appreciated that first and second substrates 12, 114 may be coupled together using a wide variety of commercially available adhesives or with welding (heat or ultrasonic) in accordance with this disclosure.

Channel 140 is sized to promote capillary flow of liquid sample 133 across tracks 16, 18. The length and width of channel 140 define the length and width of sample site 166 and the thickness of substrate 114 defines the height of the test chamber. Sample site 166 is formed to have a length of about 4 to about 8 mm and a width of about 4 to about 5 mm. Preferably, sample site is formed to have a length of about 6 mm and a width of about 4.5 mm. The degree to which tracks 16, 18 are exposed determines the surface area of each electrode. The degree of exposure may vary as discussed above with reference to biosensor 10.

Third substrate 122 of biosensor 110 overlaps a portion of second substrate 114. Third substrate 122 has a first surface 172 and a second surface 174 facing second substrate 114. As shown in FIGS. 10–11, third substrate 122 is formed to include a sample port 168 and an air vent 170 positioned in alignment with channel 140. Sample port 168 is generally circular in shape, although it is appreciated that sample port 168 can take on a variety of shapes and sizes in accordance with this disclosure. Third substrate 122 is constructed of a material identical to second substrate 114. It is appreciated that third substrate 122, may also be constructed of a variety of materials as discussed above with reference to substrates 12, 14.

As shown in FIGS. 9–11, cover 124 is formed similarly to cover 24 except that cover 124 includes raised portion 156 that is sized to receive a sink pad 160 therein. As shown in FIG. 10, sink pad 160 is in general alignment with port 168. Sink pad 160 is formed to absorb fluid when cover 124 extends across sample port 168. Sink pad 160 is formed to absorb any liquid sample that remains over port 168 following testing. Sink pad 160 is a cellulose absorbent paper manufactured by PALL Specialty Materials, Port Washington, N.Y. As an alternative, conjugate pads can also be used as "sink pad", which are commercially available from PALL Specialty Materials, Port Washington, N.Y. Adhesive 54 is used to hold the sink pad in place on cover 124.

Alternatively, a desiccant may be permanently applied to either cover 124 or to third substrate 122. A suitable desiccant removes moisture from reagent 120 when cover 124 is in a closed position, sealed against third substrate 122. Non-limiting examples of desiccants include alumina gel, silica gel, a molecular sieve type 3A or 4A, or calcium sulfate. Preferably, desiccant is DesiMax™ SLF Desiccant in tape form, which is commercially available from Multisorb Technologies, Inc., Buffalo, N.Y.

Cover 124 is releasably and recloseably coupled to third substrate 122. As shown in FIG. 10, fixed end 42 of cover 124 is affixed to third substrate 122 and adhesive 152 releasably secures middle portion 46 of cover 124 to third substrate 122. Adhesive 152 also creates an initial seal between cover 124 and third substrate 122 about sample site 166. Adhesive 152 is formed similarly to adhesive 52, except that adhesive 152 is applied about raised portion 156 and air vent 170.

Adhesive 152 is distributed over first surface 34 of second substrate 14 and/or the adjacent bottom side 28 of middle portion 46 spaced-apart from adhesive 50. The adhesive bond between middle portion 46 and third substrate 122 is broken once just prior to use. Thus, a seal is established between cover 124 and third substrate 122 around reagent 120 during storage of biosensor 10. As shown in FIG. 11, once seal is broken, a film 157 is generally left on third substrate 122 and/or cover 124 such that adhesive 152 will not reseal cover 124 and third substrate 122.

Biosensor 110 is manufactured in a manner similar to biosensor 10 except sink pads are situated in a roll. The roll of sink pads is punched, coated with an adhesive, and placed at the location of raised portion of cover 124 so that sink pad 160 will face third substrate 122.

In use, the user lifts pull tab 48 of cover 124 to separate middle portion 46 of cover 124 from second and third substrates 114, 122 and open sample port 168 to view. Liquid sample 133 is then deposited into sample port 168. Sample 133 travels and spreads through channel 140 across reagent 120 and tracks 16, 18. The reaction between the analyte and reagent 20 is the same as that described above. Once the concentration of the analyte is determined, the user presses adhesive 54 onto third substrate 122 so that cover 124 extends across sample port 168. Thus, recloseable cover 124 provides a protective covering for sample port 168 during storage before use and prior to disposal following completion of the assay to seal the liquid sample 133 in biosensor 110 to maintain a hygienic condition after use. Sink pad takes up or absorbs liquid sample 133 that remains in contact with cover 124 following use of biosensor 110.

Although the invention has been described in detail with reference to a preferred embodiment, variations and modifications exist within the scope and spirit of the invention as described and defined in the following claims.

What is claimed is:

1. A recloseable biosensor comprising:
   a substrate formed to include a sample site,
   a cover including first and second ends and a middle portion between the ends, the middle portion extending over the sample site,
   a first adhesive permanently coupling the first end of the cover to the substrate, and
   a second adhesive differing from the first adhesive that is releasably and recloseably coupling the middle portion to the substrate.

2. The biosensor of claim 1, wherein the releasable, resealable adhesive is adhered to the middle portion of the cover.

3. The biosensor of claim 1, wherein the cover includes a tab.

4. The biosensor of claim 3, wherein the releasable, resealable adhesive is spaced-apart from the tab.

5. The biosensor of claim 1, wherein the middle portion includes a sink pad.

6. The biosensor of claim 1, wherein the middle portion includes first and second sections that are foldable relative to one another.

7. A recloseable biosensor comprising:

a substrate formed to include a sample site, a reagent positioned at the sample site, a cover extending across the reagent, the cover including a fixed end, an opposite free end, and a middle portion, a first adhesive permanently coupling the fixed end to the substrate, and a second adhesive differing from the first adhesive that is releasably and recloseably coupling the middle portion to the substrate.

8. The biosensor of claim 7, wherein the free end includes a tab.

9. The biosensor of claim 7, wherein the releasable, resealable adhesive is permanently adhered to the middle portion of the cover.

10. The biosensor of claim 7, further comprising a sink pad positioned between the middle portion and the substrate.

11. A recloseable biosensor comprising:

a substrate, a reagent positioned on the substrate, an openable and recloseable cover including a fixed end coupled to the substrate, an opposite free end, and a middle portion extending between the opposite ends across the reagent, said cover being operative to selectively block access to the reagent, first and second adhesives coupling the middle portion to the substrate, the first adhesive being spaced-apart from the fixed end and the second adhesive differing from the first adhesive and being a pressure-sensitive, releasable, resealable adhesive.

12. The biosensor of claim 11, wherein the free end includes a tab.

13. The biosensor of claim 11, wherein the releasable, resealable adhesive is permanently adhered to the middle portion of the cover.

14. The biosensor of claim 11, further comprising a sink pad positioned between the middle portion and the substrate.

* * * * *